United States Patent [19]

Foure et al.

[11] 4,307,028

[45] Dec. 22, 1981

[54] PREPARATION OF ORGANO-TIN COMPOUNDS

[75] Inventors: Michel Foure, Artix; Jean-Yves Le Moal, Mourenx, both of France

[73] Assignee: Societe Nationale Elf Aquitaine, France

[21] Appl. No.: 145,678

[22] Filed: May 1, 1980

[30] Foreign Application Priority Data

May 4, 1979 [FR] France .................................. 79 11283

[51] Int. Cl.³ .............................................. C07F 7/22
[52] U.S. Cl. .................................................. 260/429.7
[58] Field of Search ...................................... 260/429.7

[56] References Cited

U.S. PATENT DOCUMENTS 2,786,813 3/1957 McDermott ..................... 260/429.7

OTHER PUBLICATIONS

Chemical Abstracts 50 9010f (1956).

*Primary Examiner*—Helen M. S. Sneed
*Attorney, Agent, or Firm*—Ostrolenk, Faber, Gerb & Soffen

[57] ABSTRACT

Preparation of organo-tin compounds, particularly mercapto-tin compounds. A metal, preferably an alkali metal, or ammonium thioxanthate is reacted with a tin salt. In a variant, the thioxanthate is produced in the reaction medium per se, starting from the corresponding trithiocarbonate and an organic halide.

15 Claims, No Drawings

PREPARATION OF ORGANO-TIN COMPOUNDS

DESCRIPTION

The invention relates to the preparation of organic compounds of tin, more particularly derivatives which include sulphur in their molecule. It also relates to the preparation of mercaptotin compounds.

Organic compounds of tin have important industrial uses at this time and are produced in considerable tonnages. It is known in particular that organotin compounds are currently utilized as stabilizers for halogenovinyl resins, as biocides and as catalysts in the preparation of polyurethane foams. There is therefore a need for processes which enable organic compounds of tin to be made economically and in a suitable state of purity. This applies particularly to organotin compounds containing mercapto groups, which are especially useful for the stabilization of halogenovinyl resins. Standard methods for the preparation of mercaptotin compounds involve the action of a thiol on a tin compound. For example, in order to make a dialkyldimercaptotin, the reaction used is:

$$R_2SnCl_2 + 2\ R'SH \rightarrow R_2Sn(SR')_2 + 2\ HCl$$

which shows the necessity of consuming a mercaptan R'SH and also a base for neutralizing the HCl formed. The cost of the final product is relatively high, partly because of the high cost of the compounds R'SH of whatever kind, e.g. alkyl or aryl mercaptans, mercapto-acids, mercapto-esters, esters of mercapto-alcohols and so on.

The present invention brings about a considerable technical advance over the prior art. It renders possible the synthesis of sulfur containing organotin compounds, without the use of mercaptans and without the necessity for subsequent neutralization. The invention thus permits the manufacture of a vast range of desired products more conveniently and at lower net cost.

The invention results from the discovery of a new and unexpected reaction, which allows one or more sulphur containing groups to be attached to a tin atom by the reaction of a thioxanthate with a tin salt.

Thus, the process according to the invention comprises reacting a tin salt with a thioxanthate of a metal or of ammonium, the metal preferable being an alkali metal, particularly sodium or potassium.

Designating the metal atom or the NH$_4$ as M and the organic radical of the thioxanthate by R', the reaction according to the invention may be written as follows, in the case of a tin salt of the anion X, optionally carrying an organic group R:

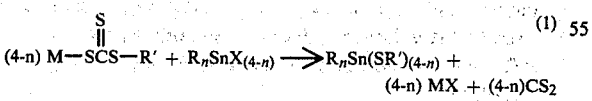

(1)

$$(4-n)\ M-\overset{\overset{\displaystyle S}{\|}}{S}CS-R' + R_nSnX_{(4-n)} \rightarrow R_nSn(SR')_{(4-n)} + (4-n)\ MX + (4-n)CS_2$$

where n is an integral number from 1 to 3 or 0.

When the tin salt used does not bear an organic radical R, that is to say when n=0, the reaction leads to a compound containing 4 organic groups R', namely Sn(SR')$_4$, according to the scheme:

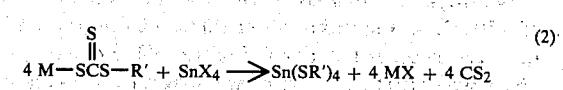

(2)

$$4\ M-\overset{\overset{\displaystyle S}{\|}}{S}CS-R' + SnX_4 \rightarrow Sn(SR')_4 + 4\ MX + 4\ CS_2$$

In the tin compounds utilized, R is an alkyl group, such as methyl, ethyl, n-propyl, iso-propyl, n-butyl, iso-butyl, sec-butyl, t-butyl, hexyl, octyl, lauryl or stearyl. R can also be a substituted group such as beta-carbo-alkoxy-ethyl, 2-oxo-butyl, 3-oxopentyl, 2-ethoxy-ethyl, etc., that means an oxo-alkyl or carbalkoxy-alkyl having 4 to 24 carbon atoms.

The anion X can be any non-oxidizing, mineral or organic anion, preferably being halogen. For both chemical and economical reasons, the anion Cl$^-$ is the one most indicated.

As regards the group R' of the thioxanthate, it may be constituted by an alkyl, cycloalkyl, alkenyl, aralkyl, carbo-alkoxyalkyl, oxo-alkyl, or an alkyl or aryl alkenyl-carboxylate; the alkyls and alkenyls involved may have more, particularly 1 to 18 carbon atoms and the aryls 6 to 12 C. Very usefully R' may be constituted by an ester moiety such as alkyl or aryl alkenyl-carboxylate, that means a group —(CH$_2$)$_m$COOR'', where m is preferably an integer of 1 to 4, R'' being a C$_1$ to C$_{18}$ radical, which group forms with a sulfur atom the above —SR' mercapto-ester group.

Thus, for example R' can be hexyl methylenecarboxylate, lauryl ethylene-carboxylate, ethyl-hexyl acetate (that is to say, methylene carboxylate) or isooctyl acetate.

To illustrate the reaction (1) above given in general terms, reference can be made for example to the preparation of n-hexyl-diethyl-tin-mercaptopropionate starting from sodium thioxanthate, the group R' of which is hexyl ethylene-carboxylate:

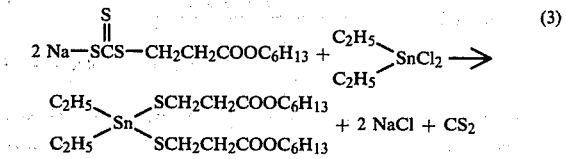

(3)

$$2\ Na-\overset{\overset{\displaystyle S}{\|}}{S}CS-CH_2CH_2COOC_6H_{13} + \underset{C_2H_5}{\overset{C_2H_5}{\diagdown}}SnCl_2 \rightarrow$$

$$\underset{C_2H_5}{\overset{C_2H_5}{\diagdown}}Sn\underset{SCH_2CH_2COOC_6H_{13}}{\overset{SCH_2CH_2COOC_6H_{13}}{\diagup}} + 2\ NaCl + CS_2$$

A tin mono-mercaptide can also be obtained, by utilizing one single mole of the thioxanthate.

The reaction according to the invention may be carried out at temperatures of 0° to 100° C., is preferably between 10° and 70° C.

As already indicated above, the considerable advantage of this process is that there is no need to use a mercaptan, as the desired organic group, —SR', is supplied by the thioxanthate. The latter can be obtained industrially in an easy and economical manner, by the known reaction of a trithiocarbonate with an organic halide. A metal or ammonium trithiocarbonate can be produced by the action of the corresponding sulphide on carbon disulphide, according to the reaction:

$$CS_2 + M_2S \rightarrow CS_3M_2 \qquad (4)$$

where M designates a cation, generally Na, K or NH$_4$. This operation is preferably effected in water, the velocity of the reaction being increased by the addition of a phase transfer catalyst, for example tri-isooctylmethyl-ammonium chloride; the operation may also be effected in mixtures of solvents, such as water/alcohol, water/dioxane and the like.

The conversion of trithiocarbonate to thioxanthate is also easy and economical. It takes place when the trithiocarbonate is reacted with a halogenated compound R'X, in which R' can be any organic radical, in particular of the types indicated above by way of example. X is a halogen, particularly Cl, Br, or I, chlorine naturally being the most practical. The following illustrates this reaction:

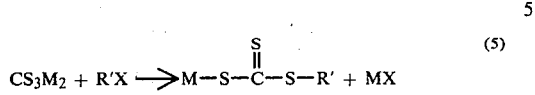  (5)

This reaction takes place well in a medium containing water, for example a water/alcohol, water/dioxane or similar mixture.

Thus, the thioxanthate obtained in reaction (5) can advantageously be employed for carrying out the indicated reactions (1) to (3) above.

Although the preparation of thioxanthate, starting from carbon disulphide and a metal sulphide (reaction 4), followed by the conversion of trithiocarbonate into the thioxanthate according to reaction (5), is particularly suitable for carrying out the invention, this is not restricted to such a method of preparation of the thioxanthate. The process applies, whatever the way in which the thioxanthate is prepared.

According to a very advantageous variant of the process of the invention, the thioxanthate is produced in situ, starting from a trithiocarbonate. That is, instead of preparing the thioxanthate in advance, a trithiocarbonate is reacted directly with an organic halide and then with a tin salt. The reaction (6) below illustrates this variant, in the case of a dialkyl tin halide ($R_2SnX_2$).

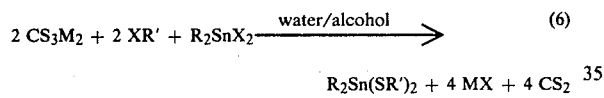  (6)

This operation takes place well in a polar solvent, particularly an alcohol such as water containing methanol.

As the reactions indicated above show, the carbon disulphide which serves to form the initial trithiocarbonate is freed during the final reaction, giving the desired organotin compound. The $CS_2$ can thus be recovered for re-use in a further preparation of the trithiocarbonate, which contributes greatly to making the process of the invention economical.

In a variation of the process, the carbon disulphide can be recovered even before the reaction with the tin salt is carried out. For this, the thioxanthate is treated with a non oxidizing acid, preferably HCl, which has the effect of liberating the $CS_2$, which is then separated. The selected tin salt is added to the remaining medium and the same tin derivative as in the right-hand half of equation (1) is obtained.

Stabilization tests on polyvinyl chloride effected with the organotin compounds prepared according to the invention show that these compounds are as effective as the corresponding compounds of the known art.

In order to have products which are sufficiently pure and to avoid the slight yellow colouration which can be given by the presence of a small quantity of the symmetrical organic trithiocarbonate, rapid treatment under vacuum of the thioxanthate utilized is sufficient. This treatment consists particularly in maintaining the thioxanthate under a vacuum of about 1 torr for 30 to 60 minutes at ordinary temperature from 25° C. to 30° C.

The non-limitative examples which follow illustrate the invention.

EXAMPLE 1

Preparation of sodium isooctyloxy-carbonyl-methylthioxanthate

In a double-walled glass reactor equipped with a stirring system, a thermometer, an equilibrated bromine ampoule and a condenser surmounted with a gas-lock, 108.2 g of a 35.26% aqueous solution of sodium trithiocarbonate (0.25 mole), 50 ml of methanol and 25.3 g of water were placed. 51.5 g of isooctylchloroacetate (0.25 mole) diluted in 25 ml of methanol was then added dropwise, while maintaining the temperature of the reaction mixture from 15° to 20° C. At the end of the addition, the mixture was stirred for 1 hour at the same temperature. A two-phase mixture was obtained.

EXAMPLE 2

Preparation of sodium (2-ethyl-hexyloxy-carbonyl)methyl thioxanthate

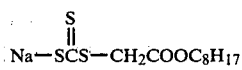

The mode of operation was exactly the same as in Example 1, except that the isooctyl-chloroacetate was replaced with 2-ethyl-hexyl-chloroacetate.

EXAMPLE 3

Preparation of dibutyltin-bis(2-ethyl-hexyl-mercaptoacetate)

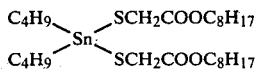

A slight excess of 12 N hydrochloric acid (d=1.19) was added dropwise in the same reactor to the thioxanthate prepared in Example 2, while maintaining the temperature at 20° to 25° C. The pH of the solution was monitored by means of a pH meter. The initial pH was 10.6 and the addition was stopped when the pH attained a value of the order of 5 to 6. The $CS_2$ formed was separated, while the organic phase was extracted with ether and then dried over calcium chloride. The solvent and the remainder of the carbon disulphide were evaporated off. A yellow product was obtained with a yield of 95%; it was constituted essentially by ethyl-hexyl-thioglycolate.

8.3 g (0.142 mole) of a 29.1% ammonia solution 14 g (0,77 mole) of water and 20 g (0.066 mole) of dibutyl-dichlorotin were introduced into a 500 ml flask equipped with a magnetic stirrer and a thermometer. 27.8 g (0.133 mole) of the ethyl-hexyl-thioglycolate previously obtained was then added dropwise at 45°-50° C. At the end of the addition, the reaction mixture was taken to 60°-65° C. for one hour. The organic phase was extracted with ether and dried over calcium chloride. 40.3 g of a yellow product was obtained.

EXAMPLE 4

Preparation of dibutyltin bis(isooctyl-mercaptoacetate)

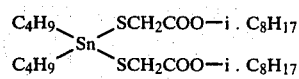

To the thioxanthate solution prepared in Example 1, 38 g (0.125 mole) of $Bu_2SnCl_2$ was added in the same reactor at 14° to 18° C. The colour changed from reddish-orange to yellow.

The methanol and the carbon disulphide were eliminated under vacuum and then the solution was extracted with ether. The organic phase was washed twice with 50 ml water and then dried over sodium sulphate. Finally, the solvent was evaporated off under vacuum. 73.6 g of a yellow liquid was obtained.

EXAMPLE 5

Preparation of dibutyltin-bis(2-ethyl-hexyl-mercaptoacetate)

The mode of operation was the same as that of Example 4, the initial thioxanthate having been prepared according to Example 2. 76.4 g of a yellow liquid was obtained.

EXAMPLE 6 Preparation of dibutyltin-bis(isooctyl-mercaptoacetate).

The mode of operation was the same as that of Example 4, except for the reaction temperature, which was maintained at 45° C. for three hours. 78.5 g of a yellow liquid was obtained.

EXAMPLE 7

Preparation of dibutyltin-bis(2-ethyl-hexyl-mercaptoacetate).

The mode of operation was the same as that of Example 4, except for the reaction temperature, which was maintained at 45° C. for three hours. 79.7 g of a yellow liquid was obtained.

The products obtained in Examples 4, 5, 6 and 7 were tested as stabilizers for PVC in comparison with pure dibutyltin-bis(2-ethyl-hexyl-mercaptoacetate). These comparative tests of the stabilization of polyvinyl chloride were effected by calendering a resin of a viscosity co-efficient K=56 in a mixer at 185° C. The concentration of stabilizer was 0.3 part by weight per 100 parts of resin. The results obtained were as follows.

| STABILIZER | APPEARANCE OF COLOUR (minutes) | |
| --- | --- | --- |
|  | Clear yellow | Dark brown |
| Pure $Bu_2Sn(SCH_2CO_2i$ . octyl$)_2$ (reference) | 2 | 12 |
| Product of Example 4 | 1-2 | 12 |
| Product of Example 5 | 1-2 | 12 |
| Product of Example 6 | 1-2 | 12 |
| Product of Example 7 | 2 | 12 |

It can be seen that the organotin compounds obtained by the process of the invention stabilize polyvinyl chloride in the same manner as the standard stabilizer.

EXAMPLE 8

Preparation of dibutyltin-bis(2-ethyl-hexyl-mercaptoacetate) by the variant in which the thioxanthate is produced in situ.

110.1 g of a 35.40% aqueous solution of sodium trithiocarbonate (0.25 mole) and 50 ml of methanol were introduced into a two-walled glass reactor equipped with an agitation system, a thermocouple thermometer, an equilibrated bromine ampoule and a condenser surmounted with a gas-lock. 51.5 g of isooctyl-chloroacetate (0.25 mole) diluted in 25 ml of methanol was then added dropwise, while maintaining the temperature of the reaction mixture at 15° to 20° C. After the end of the addition, the mixture was allowed to agitate for 1 hour at the same temperature. An orange phase and a salt deposit were obtained. About 40% by weight of the solution was eliminated by subjecting it to vacuum at 25° C. 41.8 g (0.137 mole) of $Bu_2SnCl_2$ was then added and the yellow colour disappeared. After filtering off the salt formed, the solution was extracted with 50 ml of ether, washed with water and dried over sodium sulphate. Evaporation of the solvent left 63.2 g of a colourless liquid.

The product obtained gave practically the same results as pure dibutyltin-bis(2-ethyl-hexyl mercaptoacetate) in the stabilization of polyvinyl chloride.

On the other hand, on a plastograph (200° C., v=50 rpm), the product obtained in Example 8 appeared to be strictly identical with the commercial product, from the standpoint of viscosity control.

We claim:

1. A method of producing an organic tin compound having at least one sulfur atom in its molecule, which comprises reacting in an aqueous environment a thioxanthate of the formula

where M is a cation selected from the group consisting of Na, K and $NH_4$, R' being a radical selected from the group consisting of alkyl, cycloalkyl, alkenyl, aralkyl, carbo-alkoxyalkyl, oxo-alkyl, alkyl alkenylcarboxylate and aryl alkenyl-carboxylate, the alkyl and alkenyl having 1 to 18 carbon atoms and the aryl 6 to 12 carbon atoms, with a tin compound $$R_nSnX_{(4-n)}$$

R being selected from the group consisting of $C_1$ to $C_{18}$ alkyl, $C_4$ to $C_{24}$ oxo-alkyl and $C_4$ to $C_{24}$ carbalkoxyalkyl, n is 0 or an integer of 1 to 3, and X is a non-oxidizing anion, so as to split the thioxanthate to free carbon disulfide from it, separating the carbon disulfide thus freed, and recovering the organic sulfur containing tin compound formed from the reaction medium.

2. Method according to claim 1, wherein the thioxanthate and the tin compound are reacted in a water containing organic solvent at a temperature of 10° to 70° C.

3. Method according to claim 1, wherein the thioxantate is produced in a mixture of methanol and water by reacting a trithiocarbonate of M with an organic halocompound R'X, where X is selected from the group consisting of Cl, Br and I, and then added with the tin compound, and wherein the resulting product is solvent extracted from the reaction medium.

4. Method according to claim 1, wherein the thioxantate is produced in a mixture of dioxane and water by reacting a trithiocarbonate of M with an organic halocompound R'X, where X is selected from the group consisting of Cl, Br and I, and then added with the tin compound, and wherein the resulting product is solvent extracted from the reaction medium.

5. Method according to claim 3, wherein the reaction medium of the thioxanthate production is concentrated by distilling off a part of the methanol and water, before mixture with the tin compound.

6. Method according to claim 4, wherein the reaction medium of the thioxanthate production is concentrated by distilling off a part of the dioxane and water, before mixture added with the tin compound.

7. Method according to claim 3, wherein the freed carbon disulfide is used to prepare trithiocarbonate by the reaction $CS_2 + M_2S \rightarrow CS_3M_2$ in aqueous medium, thus forming a cyclic process.

8. Method according to claim 1, wherein the thioxanthate, before being reacted with the tin compound, is treated with a non oxidizing acid in an aqueous solvent to separate carbon disulfide from the thioxanthate.

9. Method according to claim 2, wherein the thioxanthate, before being reacted with the tin compound, is treated with a non oxidizing acid in a aqueous solvent to separate carbon disulfide from the thioxanthate.

10. Method according to claim 3, wherein the thioxanthate, before being reacted with the tin compound, is treated with a non oxidizing acid in an aqueous solvent to separate carbon disulfide from the thioxanthate.

11. Method according to claim 4, wherein the thioxanthate, before being reacted with the tin compound, is treated with a non oxidizing acid in an aqueous solvent to separate carbon disulfide from the thioxanthate.

12. Method according to claim 1, in which the thioxanthate used is first kept at 25° to 30° C., under a depression of about 1 torr for 30 to 60 minutes to avoid the colouring of the final reaction product.

13. Method according to claim 2, in which the thioxanthate used is first kept at 25° to 30° C., under a depression of about 1 torr for 30 to 60 minutes to avoid the colouring of the final reaction product.

14. Method according to claim 3, in which the thioxanthate used is first kept at 25° to 30° C., under a depression of about 1 torr for 30 to 60 minutes to avoid the colouring of the final reaction product.

15. Method according to claim 4, in which the thioxanthate used is first kept at 25° to 30° C., under a depression of about 1 torr for 30 to 60 minutes to avoid the colouring of the final reaction product.

* * * * *